United States Patent
Shaikh et al.

(10) Patent No.: US 9,156,805 B2
(45) Date of Patent: Oct. 13, 2015

(54) OXIDATIVE PURIFICATION METHOD FOR PRODUCING PURIFIED DRY FURAN-2,5-DICARBOXYLIC ACID

(71) Applicant: Eastman Chemical Company, Kingsport, TN (US)

(72) Inventors: Ashfaq Shaikh, Kingsport, TN (US); Kenny R. Parker, Afton, TN (US); Mesfin Ejerssa Janka, Kingsport, TN (US); Lee R. Partin, Kingsport, TN (US)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 0 days.

(21) Appl. No.: 14/084,165

(22) Filed: Nov. 19, 2013

(65) Prior Publication Data

US 2014/0142328 A1    May 22, 2014

Related U.S. Application Data

(60) Provisional application No. 61/728,317, filed on Nov. 20, 2012.

(51) Int. Cl.
*C07D 307/34* (2006.01)
*C07D 307/68* (2006.01)

(52) U.S. Cl.
CPC .................................. *C07D 307/68* (2013.01)

(58) Field of Classification Search
CPC ................................................... C07D 307/34
USPC .................... 549/29, 483, 429, 485
See application file for complete search history.

(56) References Cited

U.S. PATENT DOCUMENTS

| | | | |
|---|---|---|---|
| 2,797,197 A | 6/1957 | Thompson et al. | |
| 3,203,963 A | 8/1965 | Hales et al. | |
| 3,326,944 A | 6/1967 | Lew | |
| 4,977,283 A | 12/1990 | Leupold et al. | |
| 6,737,481 B1 | 5/2004 | Kurian et al. | |
| 7,052,764 B2 | 5/2006 | Chang et al. | |
| 7,385,081 B1 | 6/2008 | Gong | |
| 7,411,078 B2 | 8/2008 | Miura et al. | |
| 7,572,925 B2 * | 8/2009 | Dumesic et al. | 549/488 |
| 7,700,788 B2 * | 4/2010 | Lilga et al. | 549/484 |
| 8,183,020 B2 * | 5/2012 | Hanke | 435/126 |
| 8,193,381 B2 * | 6/2012 | Lilga et al. | 549/485 |
| 8,193,382 B2 * | 6/2012 | Lilga et al. | 549/489 |
| 8,748,479 B2 | 6/2014 | Shaikh et al. | |
| 8,772,513 B2 | 7/2014 | Janka et al. | |
| 8,791,277 B2 | 7/2014 | Janka et al. | |
| 8,791,278 B2 | 7/2014 | Shaikh et al. | |
| 8,796,477 B2 | 8/2014 | Janka et al. | |
| 8,809,556 B2 | 8/2014 | Janka et al. | |
| 8,846,960 B2 | 9/2014 | Janka et al. | |
| 8,916,719 B2 | 12/2014 | Shaikh et al. | |
| 8,916,720 B2 | 12/2014 | Shaikh et al. | |
| 8,969,404 B2 | 3/2015 | Janka et al. | |
| 2003/0055271 A1 | 3/2003 | Grushin et al. | |
| 2006/0205977 A1 | 9/2006 | Sumner, Jr. et al. | |
| 2007/0232815 A1 | 10/2007 | Miura et al. | |
| 2009/0124829 A1 | 5/2009 | Gong | |
| 2009/0131690 A1 | 5/2009 | Gruter et al. | |
| 2009/0156841 A1 | 6/2009 | Sanborn et al. | |
| 2009/0326262 A1 | 12/2009 | Wan | |
| 2010/0210867 A1 | 8/2010 | Bustamante et al. | |
| 2011/0092720 A1 | 4/2011 | Yutaka et al. | |
| 2012/0302768 A1 | 11/2012 | Janka et al. | |
| 2012/0302769 A1 | 11/2012 | Janka et al. | |
| 2012/0302770 A1 | 11/2012 | Janka et al. | |
| 2012/0302771 A1 | 11/2012 | Janka et al. | |
| 2012/0302772 A1 | 11/2012 | Shaikh et al. | |
| 2012/0302773 A1 | 11/2012 | Janka et al. | |
| 2013/0345452 A1 | 12/2013 | Janke et al. | |
| 2014/0024844 A1 | 1/2014 | Janka et a. | |
| 2014/0235880 A1 | 8/2014 | Shaikh et al. | |
| 2014/0364633 A1 | 12/2014 | Janke et al. | |

FOREIGN PATENT DOCUMENTS

| | | |
|---|---|---|
| CS | 87340 | 7/1959 |
| EP | 1 834 951 A1 | 9/2007 |
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |

(Continued)

OTHER PUBLICATIONS

Notice of Allowance dated May 13, 2014 received in co-pending U.S. Appl. No. 13/758,088.
Copending U.S. Appl. No. 14/282,360, filed May 20, 2014, Janka et al.
Notice of Allowance dated Aug. 8, 2014 received in co-pending U.S. Appl. No. 13/228,809.
Office Action dated Sep. 26, 2014 received in co-pending U.S. Appl. No. 13/13/758,072.
Notice of Allowance dated Oct. 9, 2014 received in co-pending U.S. Appl. No. 13/798,257.
Notice of Allowance dated Oct. 15, 2014 received in co-pending U.S. Appl. No. 13/798,235.
Notice of Allowance dated Dec. 17, 2014 received in co-pending U.S. Appl. No. 13/758,080.

(Continued)

*Primary Examiner* — Golam M M Shameem
(74) *Attorney, Agent, or Firm* — Steven A. Owen

(57) ABSTRACT

Disclosed is a process to produce a dry purified carboxylic acid product comprising furan-2,5-dicarboxylic acid (FDCA). The process comprises oxidizing a feed stream comprising at least one oxidizable compound to generate a crude carboxylic acid slurry comprising FDCA, removing impurities from a crude carboxylic acid slurry via oxidative purification in a low temperature post-oxidation zone to form a low impurity slurry stream. The low impurity slurry stream is further treated in a high temperature post oxidation zone to produce a secondary oxidation slurry stream which is routed to a crystallization zone to from a crystallized slurry stream.

11 Claims, 1 Drawing Sheet

(56) References Cited

FOREIGN PATENT DOCUMENTS

| JP | 2009-013079 A | 1/2009 |
|---|---|---|
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | WO 2012/161968 A1 | 11/2012 |
| WO | 2014/193634 A1 | 12/2014 |
| WO | 2014/197195 A2 | 12/2014 |

OTHER PUBLICATIONS

Notice of Allowance dated Apr. 1, 2014 received in co-pending U.S. Appl. No. 13/758,080.
Notice of Allowance dated Apr. 1, 2014 received in co-pending U.S. Appl. No. 13/758,070.
Office Action dated Apr. 17, 2014 received in co-pending U.S. Appl. No. 13/758,072.
Copending U.S. Appl. No. 14/259,754, filed Apr. 23, 2014, Ashfaq Shaikh et al.
Office Action dated Apr. 30, 2014 received in co-pending U.S. Appl. No. 13/798,235.
Office Action dated Apr. 25, 2014 received in co-pending U.S. Appl. No. 13/228,797.
Office Action dated Apr. 25, 2014 received in co-pending U.S. Appl. No. 13/228,809.
Office Action dated Apr. 25, 2014 received in co-pending U.S. Appl. No. 13/798,257.
Notice of Allowance dated Apr. 28, 2014 received in co-pending U.S. Appl. No. 13/228,813.
Notice of Allowance dated Apr. 28, 2014 received in co-pending U.S. Appl. No. 13/228,803.
Notice of Allowance dated May 1, 2014 received in co-pending U.S. Appl. No. 13/228,799.
Office Action dated May 29, 2014 received in co-pending U.S. Appl. No. 13/228,816.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,692, filed Jun. 27, 2014, Janka et al.
Copending U.S. Appl. No. 14/317,782, filed Jun. 27, 2014, Parker et al.
Copending U.S. Appl. No. 14/317,875, filed Jun. 27, 2014, Janka et al.
Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.
Lewkowski, J.; "Synthesis, Chemistry and Applications of 5-Hydroxymethylfurfural and its Derivatives," ARKIVOC, 2001, pp. 17-54.
Zakharov, I. V., "Mechanism of Initiation and Inhibition by Mn(II) in Hydrocarbon Oxidation in the Presence a Cobalt-Manganese Bromide Catalyst," Kinetics and Catalysis, 1998, vol. 39, No. 4, pp. 485-492.
Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.
Copending U.S. Appl. No. 13/228,816, filed Sep. 9, 2011, Mesfin Ejerssa Janka, et al.
Copending U.S. Appl. No. 13/228,799, filed Sep. 9, 2011, Mesfin Ejerssa Janka, et al.
Copending U.S. Appl. No. 13/228,809, filed Sep. 9, 2011, Mesfin Ejerssa Janka, et al.
Copending U.S. Appl. No. 13/228,803, filed Sep. 9, 2011, Mesfin Ejerssa Janka, et al.
Copending U.S. Appl. No. 13/228,797, filed Sep. 9, 2011, Mesfin Ejerssa Janka, et al.
Copending U.S. Appl. No. 13/228,813, filed Sep. 9, 2011, Ashfaq Shaikh, et al.
PCT International Search Report and Written Opinion dated Jul. 27, 2012 for International Application No. PCT/US2012/037223.
PCT International Search Report and Written Opinion dated Aug. 7, 2012 for International Application No. PCT/US2012/037218.
PCT International Search Report and Written Opinion dated Jul. 27, 2012 for International Application No. PCT/US2012/037204.
PCT International Search Report and Written Opinion dated Jul. 27, 2012 for International Application No. PCT/US2012/037206.
PCT International Search Report and Written Opinion dated Aug. 3, 2012 for International Application No. PCT/US2012/037210.
Copending U.S. Appl. No. 13/553,976, filed Jul. 20, 2012, Mesfin Ejerssa Janka, et al.
PCT International Search Report and Written Opinion dated Aug. 23, 2012 for International Application No. PCT/US2012/037228.
Chheda et al., "Production of 5-hydromethylfurfural and furfural by dehydration of biomass-derived mono- and poly-saccharides." Green Chemistry, vol. 9, pp. 342-350 (2007).
Werpy et al., "Top Value Added Chemicals from Biomass" DOE (Pacific NW National Laboratory) (Aug. 2004).
Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).
Manasek, Z., "Modification of a Fiber-Forming Polyester Based on 2,5-Furandicarboxylic Acid", Mar. 20, 1963, pp. 35-38, UDC 677.465.
Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.
Copending U.S. Appl. No. 13/758,070, filed Feb. 4, 2013, Kenny Randolph Parker, et al.
Copending U.S. Appl. No. 13/758,080, filed Feb. 4, 2013, Mesfin Ejerssa Janka, et al.
Office Action dated Apr. 18, 2013 received in co-pending U.S. Appl. No. 13/228,797.
Office Action dated Apr. 18, 2013 received in co-pending U.S. Appl. No. 13/228,813.
Office Action dated Apr. 29, 2013 received in co-pending U.S. Appl. No. 13/228,799.
Office Action dated May 31, 2013 received in co-pending U.S. Appl. No. 13/228,803.
Office Action dated Jun. 6, 2013 received in co-pending U.S. Appl. No. 13/228,809.
Office Action dated Jun. 6, 2013 received in co-pending U.S. Appl. No. 13/228,816.
PCT International Search Report and Written Opinion dated Jul. 29, 2013 for International Application No. PCT/US2013/044935.
PCT International Search Report and Written Opinion dated Aug. 9, 2013 for International Application No. PCT/US2013/044932.
Office Action dated Sep. 30, 2013 received in co-pending U.S. Appl. No. 13/758,070.

(56) References Cited

OTHER PUBLICATIONS

Office Action dated Sep. 30, 2013 received in co-pending U.S. Appl. No. 13/758,080.
Moldenhauer, et al., "Beitrage zur Furanchemie I", Justus Liebigs Annalen Der Chemie, vol. 580, 1953, pp. 169-190.
Office Action dated Oct. 25, 2013 received in co-pending U.S. Appl. No. 13/228,813.
PCT International Search Report and Written Opinion dated Oct. 31, 2013 for International Application No. PCT/US2013/050799.
Office Action dated Nov. 5, 2013 received in co-pending U.S. Appl. No. 13/228,797.
Office Action dated Nov. 8, 2013 received in co-pending U.S. Appl. No. 13/758,070.
Office Action dated Nov. 12, 2013 received in co-pending U.S. Appl. No. 13/228,799.
Office Action dated Nov. 14, 2013 received in co-pending U.S. Appl. No. 13/228,809.
Office Action dated Nov. 18, 2013 received in co-pending U.S. Appl. No. 13/758,088.
PCT International Search Report and Written Opinion dated Nov. 28, 2013 for International Application No. PCT/US2013/050794.
Office Action dated Dec. 13, 2013 received in co-pending U.S. Appl. No. 13/228,816.
Office Action dated Dec. 16, 2013 received in co-pending U.S. Appl. No. 13/553,976.
PCT International Search Report and Written Opinion dated Dec. 30, 2013 for International Application No. PCT/US2013/056362.

\* cited by examiner

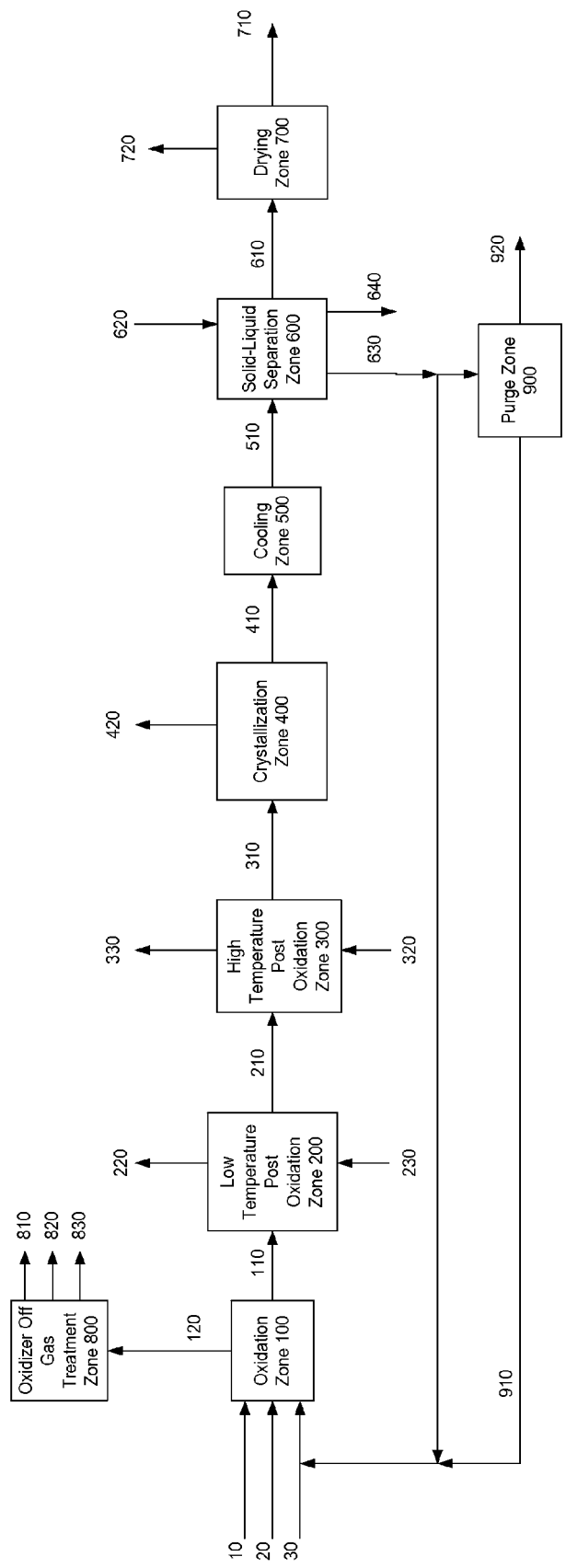

OXIDATIVE PURIFICATION METHOD FOR PRODUCING PURIFIED DRY FURAN-2,5-DICARBOXYLIC ACID

CROSS-REFERENCES TO RELATED APPLICATIONS

This application claims priority under 35 U.S.C. §119(e) to U.S. Provisional Application Ser. No. 61/728,317 filed on Nov. 20, 2012.

BACKGROUND OF THE INVENTION

Aromatic dicarboxylic acids such as terephthalic acid and isophthalic acid are used to produce a variety of polyester products, important examples of which are poly(ethylene terephthalate) and its copolymers. These aromatic dicarboxylic acids are synthesized by the catalytic oxidation of the corresponding dialkyl aromatic compounds which are obtained from fossil fuels (US 2006/0205977 A1). There is a growing interest in the use of renewable resources as feed stocks for the chemical industries mainly due to the progressive reduction of fossil reserves and their related environmental impacts.

FDCA is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) (Gandini, A.; Silvestre, A. J; Neto, C. P.; Sousa, A. F.; Gomes, M. *J. Poly. Sci. A* 2009, 47, 295). FDCA has been prepared by oxidation of 5-(hydroxymethyl) furfural (5-HMF) under air using homogenous catalysts (US2003/0055271 A1 and Partenheimer, W.; Grushin, V. V. *Adv. Synth. Catal.* 2001, 343, 102-111) but only a maximum of 44.8% yield using Co/Mn/Br catalysts system and a maximum of 60.9% yield was reported using Co/Mn/Br/Zr catalysts combination. Recently we report a process for producing furan-2,5-dicarboxylic acid (FDCA) in high yields by liquid phase oxidation of 5-HMF using Co/Mn/Br catalysts system that minimizes solvent and starting material loss through carbon burn. Heterogeneous catalysis oxidation of 5-HMF using $ZrO_2$ mixed with platinum (II) acetylacetonate in water has also been reported (U.S. Pat. No. 7,700,788 B2) but due to very low solubility of FDCA in water, this process needs to be conducted under very dilute conditions to avoid precipitation of FDCA on the catalysts surface which makes the process not economical. Another heterogeneous catalysis oxidation of 5-HMF is reported (U.S. Pat. No. 4,977,283) using molecular $O_2$ and a Pt/C catalyst. High FDCA yield was achieved but at the extra expense of feeding purified $O_2$ and continually adjusting pH via sodium hydroxide addition. The reaction product was the disodium salt of FDCA leading to a wasteful salt by-product in the conversion to FDCA. A high yield process (minimum of 90% FDCA yield), to produce a dry purified FDCA product is disclosed in this invention report.

DETAILED DESCRIPTION

One embodiment of the present invention is illustrated in FIG. 1. The present invention provides a process for producing a dry purified carboxylic acid product stream 710 comprising dry purified furan-2,5-dicarboxylic acid (FDCA) and comprises the following steps:

Step (a) comprises feeding solvent, a catalyst system, a gas comprising oxygen, and oxidizable raw material comprising at least one compound selected from the group of formula: 5-(hydroxymethyl)furfural (5-HMF), 5-HMF esters (5-R(CO)$OCH_2$-furfural where R=alkyl, cycloalkyl and aryl), 5-HMF ethers (5-R'$OCH_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters and mixed feed-stocks of 5-HMF and 5-HMF ethers and mixed feed-stocks of 5-HMF and 5-alkyl furfurals to a primary oxidation zone to generate a crude furan-2,5-dicarboxylic acid composition stream 110. Structures for the preferred oxidizable raw material compounds are outlined below:

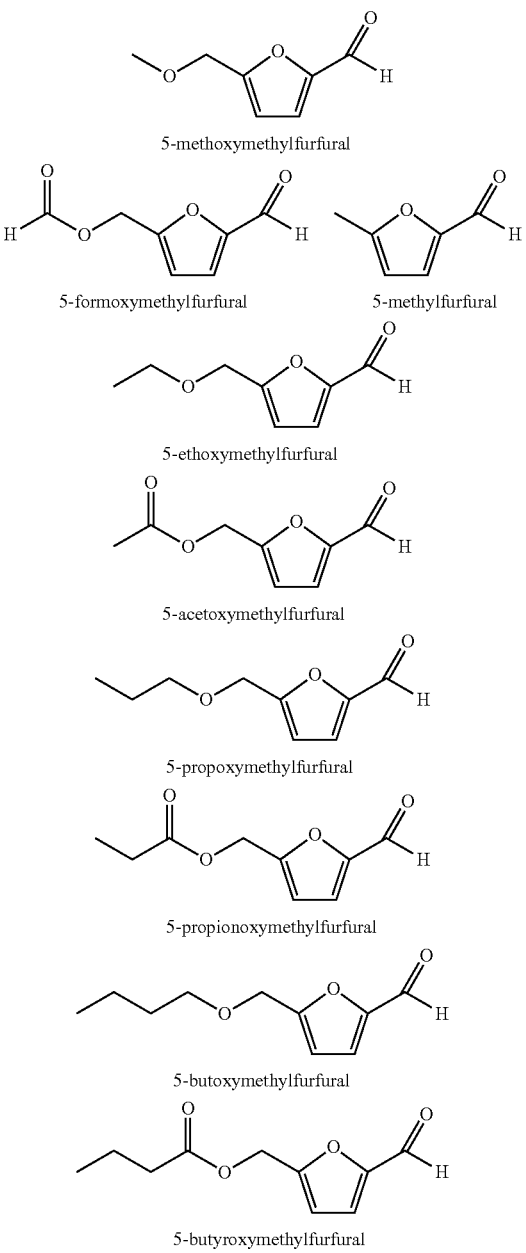

The 5-HMF or its derivatives are oxidized with elemental $O_2$ in a multi-step reaction to form FDCA with 5-formyl furan-2-carboxylic acid (FFCA) as a key intermediate.

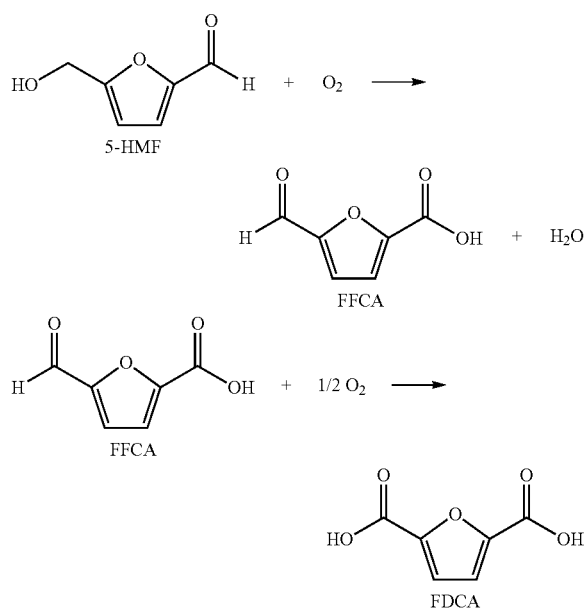

In one embodiment, streams routed to the primary oxidizer comprise gas stream 10 comprising oxygen and stream 20 comprising solvent, and oxidizable raw material. In another embodiment, streams routed to the primary oxidizer comprise gas stream 10 comprising oxygen and stream 20 comprising solvent, catalyst, and oxidizable raw material. In yet another embodiment, the oxidation solvent, gas comprising oxygen, catalyst system, and oxidizable raw materials can be fed to the primary oxidizer as separate and individual streams or combined in any combination prior to entering the primary oxidizer wherein said fed streams may enter at a single location or in multiple locations in the primary oxidizer. Suitable catalysts comprise at least one selected from, but are not limited to, cobalt, bromine and manganese compounds, which are soluble in the selected oxidation solvent. The preferred catalyst system comprises cobalt, manganese and bromine wherein the weight ratio of cobalt to manganese in the reaction mixture is from about 10 to about 400 and the weight ratio of cobalt to bromine is from about 0.7 to about 3.5. Suitable solvents include, but are not limited to, aliphatic mono-carboxylic acids, preferably containing 2 to 6 carbon atoms and mixtures thereof and mixtures of these compounds with water. Throughout the specification acetic acid will be referred to as the solvent. The temperature in the primary oxidation zone can range from 105 C to 180 C, and can preferably range from 110 C to 160 C. One advantage of the disclosed primary oxidation conditions is low carbon burn as illustrated in Table 1. Oxidizer off gas stream 120 is routed to the oxidizer off gas treatment zone to generate an inert gas stream 810, liquid stream 820 comprising water, and a recovered solvent stream 830 comprising condensed solvent. In one embodiment, at least a portion of recovered solvent stream 830 is routed to wash fed stream 620 and the combined stream is routed to the solid-liquid separation zone for the purpose of washing the solids present in the solid-liquid separation zone. In one embodiment, the inert gas stream 810 can be vented to the atmosphere. In another embodiment, at least a portion of the inert gas stream 810 can be used as an inert gas in the process for inerting vessels and or used for convey gas for solids in the process.

Step (b) comprises routing the crude carboxylic acid slurry stream 110 and gas stream 230 to low temperature post-oxidation zone 200 for oxidative purification to generate low impurity stream 210. Stream 110 was reacted with gas stream 230 comprising oxygen. In one embodiment, 230 is a part of gas stream 10 supplied to primary oxidation zone. In another embodiment, 230 is an independent gas stream. In one embodiment if gas stream 230 is a part of gas stream 10, the ratio of gas stream 10 to gas stream 230 will vary from 0.5-10%, 0.6-6% and more preferably 0.9-3%. Low temperature post-oxidation zone 200 will further oxidize unreacted intermediates in liquid phase. The reduced impurities in liquid phase of a slurry stream 210 will help reduce carbon burn in high temperature oxidation zone 300. One advantage of oxidative purification is to eliminate a liquid displacement zone that can be used to generate low impurity stream 210 resulting in reduction of relative capital and operating cost while achieving lower carbon burn. The temperature in the post-oxidation zone can range from 105 C to 180 C, and can preferably range from 110 C to 160 C. The temperature of low temperature post oxidation zone 200 should be within 10 C of primary oxidation zone 100. In one embodiment off gas stream 220 can be returned to a primary oxidation zone 100. In another embodiment, off gas stream 220 can be routed to off gas treatment zone.

Step (c) comprises oxidizing the low impurity slurry stream 210 in a high temperature post oxidation zone to form a secondary oxidation slurry stream 310. In one embodiment of the invention, the low impurity slurry stream 210 is routed to a high temperature post oxidation zone where it is heated to between about 115 degrees C. and about 220 degrees C., and preferably between about 120 degrees C. to about 200 degrees C. and further oxidized with air fed by line 320 to produce a purified slurry stream 310. The high temperature post oxidation zone comprises at least one oxidation reactor vessel. In one embodiment, the high temperature post oxidation zone can be one or more oxidation vessels. When the carboxylic acid in low impurity stream 210 is FDCA, the high temperature post oxidation zone is operated at a temperature ranging from about 115 degrees C. to about 220 degrees C., preferably between about 120 degrees C. to about 200 degrees C., and stream 210 is further oxidized with air or a source of molecular oxygen fed by line 320 to produce secondary oxidation slurry 310. Generally, oxidation in the high temperature post oxidation zone is at a higher temperature than the oxidation in the primary oxidation zone to enhance the impurity removal. In one embodiment, the high temperature post oxidation zone is operated at about 30 C, 20 C, and preferably 100 higher temperature than the oxidation temperature in the primary oxidation zone to enhance the impurity removal. The high temperature post oxidation zone can be heated directly with solvent vapor, or steam via stream 320 or indirectly by any means known in the art. Additional purification of the low impurity slurry stream 210 is accomplished in the high temperature post oxidation zone by a mechanism involving recrystallization or crystal growth and oxidation of impurities and intermediates including FFCA. One of the functions of the high temperature post oxidation zone is to convert FFCA to FDCA. FFCA is considered monofunctional relative to a polyester condensation reaction because it contains only one carboxylic acid. FFCA is present in the crude carboxylic acid stream 110 and the low impurity slurry stream 210. FFCA is generated in the primary oxidation zone because the reaction of 5-HMF to FFCA can be about eight times faster than the reaction of FFCA to the desired di-functional product FDCA. Additional air or molecular oxygen may be fed in stream 320 to the high temperature post oxidation zone in an amount necessary to oxidize a substantial portion of the partially oxidized products such as FFCA in the stream 210 to the corresponding carboxylic acid FDCA. Generally, at least 70% by weight of the FFCA present in the low impurity slurry stream 210 is converted to FDCA in the high temperature post oxidation zone. Preferably, at least 80% by weight of the FFCA present in the low impurity slurry stream 210 is converted to FDCA in the high temperature post oxidation zone, and most preferably, at least 90% by weight of the FFCA present in the low impurity slurry stream 210 is converted to FDCA in the high temperature post oxidation zone. Significant concentrations of monofunctional molecules like FFCA in the dry purified FDCA product are particularly detrimental to polymerization processes as they may act as chain terminators during the polyester condensation reaction. The amount of oxygen fed in the high temperature post oxidation zone in controlled to limit the burning of organic molecules to $CO_2$. The amount of oxygen in stream 330 is monitored and used to control the amount of oxygen fed in stream 320. Another function of the high temperature post oxidation zone is to dissolve and recrystallize solids present in the low impurity slurry stream 210 fed to the high temperature post oxidation zone. At least 10% by weight, 25% by weight, 50% by weight, and preferably at least 85% by weight of solid impurities and oxidation by-products in stream 210 feed to the high temperature post oxidation zone go into solution as the FDCA particles are dissolved and re-crystallized in the high temperature post oxidation zone. Off gas from the high temperature post oxidation zone is withdrawn via line 330 and fed to a recovery system where the solvent is removed from the off gas comprising volatile organic compounds (VOCs). VOCs including methyl bromide may be treated, for example by incineration in a catalytic oxidation unit. The high temperature post oxidation slurry 310 generated in the high temperature post oxidation zone is routed to the crystallization zone.

Step (d) comprises crystallizing the high temperature post oxidation slurry 310 in a crystallization zone to form a crystallized slurry stream 410. Generally, the crystallization zone comprises at least one crystallizer. Vapor product from the crystallization zone can be condensed in at least one condenser and returned to the crystallization zone. Optionally, the liquid from the condenser or vapor product from the crystallization zone can be recycled, or it can be withdrawn or sent to an energy recovery device. In addition, the crystallizer off gas is removed via line 420 and can be routed to a recovery system where the solvent is removed and crystallizer off gas comprising VOCs may be treated, for example by incineration in a catalytic oxidation unit. When the carboxylic acid is FDCA, the high temperature post oxidation slurry stream 310 from the high temperature post oxidation zone is fed to a crystallization zone comprising at least one crystallizer where it is cooled to a temperature between about 40.degrees C. to about 175 degrees C. to form a crystallized product 410, preferably to a temperature between about 50 degrees C. to about 170 degrees C., and most preferably from about 60 degree C. to about 165 degrees C. The crystallized product stream 410 is then routed to a cooling zone to generate a cooled crystallized slurry stream 510. The cooling of the crystallized slurry stream 410 can be accomplished by any means known in the art; typically the cooling zone comprises a flash tank. The temperature of stream 510 can range from 35 C to 160 C, 45 C to 120, and preferably from 55 C to 95 C. In another embodiment, a portion of up to 100% of the secondary oxidation slurry stream 310 is routed directly to the cooling zone, thus said portion is not subjected to a crystallization zone. In yet another embodiment, a portion of up to 100% of the crystallized slurry stream 410 routed directly to a secondary liquid displacement zone which is not illustrated in FIG. 1. Up to 100% of the slurry effluent comprising FDCA from a secondary liquid displacement zone can be routed to the solid-liquid separation zone and or routed directly to the cooling zone. The function of the secondary liquid displacement zone is to displace a portion of solvent in the crystallized slurry stream 410 comprising fresh solvent and or water wherein a portion must be greater than 5 weight %. The secondary liquid displacement zone is separate and distinct from the liquid displacement zone located after the primary oxidation zone. The same type of equipment may be used for both the primary and secondary liquid displacement zones. In yet another embodiment, crystallized slurry stream 410 can be routed directly to the solid-liquid separation zone without being first processed in the cooling zone.

Step (e) comprises isolating, washing, and dewatering solids present in the cooled slurry stream 510 in the solid-liquid separation zone. These functions may be accomplished in a single solid-liquid separation device or multiple solid-liquid separation devices. The solid-liquid separation zone comprises at least one solid-liquid separation device capable of separating solids and liquids, washing solids with a wash fed stream 620, and reducing the % moisture in the washed solids to less than 30 weight %, less than 25 weight %, less than 20 weight %, less than 15 weight %, and preferably less than 10 weight %. Equipment suitable for the solid liquid separation zone can typically be comprised of, but not limited to, the following types of devices: centrifuges, cyclones, rotary drum filter, belt filters, pressure leaf filters, candle filters, etc. The preferred solid liquid separation device for the solid liquid separation zone is a rotary pressure drum filter. The temperature of cooled slurry steam 510 which is routed to the solid-liquid separation zone can range from 50 C to 140 C, 70 C to 120 C, and is preferably from 75 C to 95 C. The wash stream 620 comprises a liquid suitable for displacing and washing mother liquor from the solids. In one embodiment, a suitable wash solvent comprises acetic acid and water. In another embodiment, a suitable solvent comprises water up to 100% water. The temperature of the wash solvent can range from 20 C to 120 C, 40 C and 110 C, and preferably from 50 C to 90 C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3. After solids are washed in the solid liquid separation zone, they are dewatered. Dewatering involves reducing the mass of moisture present with the solids to less than 30% by weight, less than 25% by weight, less than 20% by weight, less than 15% by weight, and most preferably less than 10% by weight resulting in the generation of a purified dewatered wet cake stream 610. In one embodiment, dewatering is accomplished in a filter by passing a gas stream through the solids to displace free liquid after the solids have been washed with a wash solvent. In another embodiment, dewatering is achieved by centrifugal forces in a perforated bowl or solid bowl centrifuge. Steam 630 generated in the solid-liquid separation zone is a mother liquor stream comprising solvent, catalyst, and some impurities and oxidation by products. In one embodiment, a portion of stream 630 is routed to a purge zone and a portion is routed back to the primary oxidation zone wherein a portion is at least 5 weight %. Wash liquor stream 640 is also generated in the solid-liquid separation zone and comprises a portion of the mother liquor present in stream 510 and wash solvent wherein the ratio of mother liquor mass to wash solvent mass is less than 3 and preferably less than 2.

Step (f) comprises drying the purified dewatered wet cake stream 610 in a dryer zone to generate a dry purified FDCA product stream 710 and a vapor stream 720. In one embodiment, vapor stream 720 comprises wash solvent vapor. In another embodiment, vapor stream 720 comprises oxidation solvent and wash solvent. The drying zone comprises at least one dryer and can be accomplished by any means known in the art that is capable of evaporating at least 10% of the volatiles remaining in the purified dewatered wet cake stream 610 to produce the dry product stream comprising purified FDCA and a vapor stream 720. For example, indirect contact dryers including a rotary steam tube dryer, a Single Shaft Porcupine® dryer, and a Bepex Solidaire® dryer. Direct contact dryers including a fluid bed dryer and drying in a convey line can be used for drying to produce stream 710. The dried product stream 710 comprising purified FDCA can be a carboxylic acid composition with less than 8% moisture, preferably less than 5% moisture, and more preferably less than 1% moisture, and even more preferably less than 0.5%, and yet more preferably less than 0.1%. In another embodiment of this invention, if the liquid portion of the purified dewatered wet cake stream 610 comprises water and contains less than 0.1 weight % acetic acid, less than 500 ppm wt acetic acid, and preferably less than 200 ppm wt, the stream 610 can be fed directly to a polymerization zone without first being dried.

In an embodiment of the invention, the dried carboxylic acid stream 710 has a b* less than about 9.0. In another embodiment of the invention, the b* color of the dried carboxylic acid stream 710 is less than about 6.0. In another embodiment of the invention, the b* color of the dried carboxylic acid stream 710 is less than about 5.0. In another embodiment of the invention, the b* color of the dried carboxylic acid stream 710 is less than about 4.0. In another embodiment of the invention, the b* color of the dried carboxylic acid stream 710 is less than about 3. The b* color is one of the three-color attributes measured on a spectroscopic reflectance-based instrument. A Hunter Ultrascan XE instrument in reflectance mode is typically the measuring device. Positive readings signify the degree of yellow (or absorbance of blue), while negative readings signify the degree of blue (or absorbance of yellow).

It should be appreciated that the process zones previously described can be utilized in any other logical order to produce the purified carboxylic acid product. It should also be appreciated that when the process zones are reordered that the process conditions may change. It is also understood that all percent values are weight percents.

Step (g) in another embodiment of this invention each embodiment can optionally include an additional step comprising decolorizing of FDCA in this process or an esterified FDCA with a diol stream via hydrogenation. In one embodiment, the diol stream comprises ethylene glycol. In another embodiment, the diol stream comprises isomers of cyclohexane diol, preferably the 1-4 cyclohexane diol isomer. The decolorizing of the FDCA in this process or an esterified FDCA can be accomplished by any means known in the art and is not limited to hydrogenation. However, for example in one embodiment of the invention, the decolorizing can be accomplished by reacting a carboxylic acid that has undergone esterification treatment, for example with ethylene glycol, with molecular hydrogen in the presence of a hydrogenation catalyst in a reactor zone to produce a decolorized carboxylic acid solution or a decolorized ester product. For the reactor zone, there are no special limitations in the form or construction thereof, subject to an arrangement that allows supply of hydrogen to effect intimate contact of the carboxylic acid or ester product with the catalyst in the reactor zone.

Typically, the hydrogenation catalyst is usually a single Group VIII metal or combination of Group VIII metals. Preferably, the catalyst is selected from a group consisting of palladium, ruthenium, rhodium and combination thereof. The reactor zone comprises a hydrogenation reactor that operates at a temperature and pressure sufficient to hydrogenate a portion of the characteristically yellow compounds to colorless derivatives.

Illustrative procedure, representative of those used for the semi-batch oxidation of 5-HMF.

The invention claimed is:

1. A process to produce a purified slurry stream comprising furan-2,5-dicarboxylic acid (FDCA), said process comprising:
   (a) oxidizing in primary oxidation zone an oxidizable compound in an oxidizable raw material stream in the presence of a solvent stream, an oxidizing gas stream, and a catalyst system, wherein said oxidizable raw material stream comprises at least one compound selected from the group consisting of 5-(hydroxymethyl)furfural (5-HMF), 5-HMF esters (5-R(CO)OCH2-furfural where R=alkyl, cycloalkyl and aryl), 5-HMF ethers (5-R'OCH2-furfural, where R'=alkyl, cycloalkyl and aryl), 5-alkyl furfurals (5-R"-furfural, where R"=alkyl, cycloalkyl and aryl), mixed feedstocks of 5-HMF and 5-HMF esters, mixed feedstocks of 5-HMF and 5-HMF ethers, and mixed feedstocks of 5-HMF and 5-alkyl furfurals to produce a crude caboxylic acid composition comprising furan-2,5-dicarboxylic acid (FDCA); wherein said catalyst system comprises cobalt in a range from about 500 ppm to about 6000 ppm with respect to the weight of the liquid in the primary oxidation zone, manganese in an amount ranging from about 2 ppm to about 600 ppm by weight with respect to the weight of the liquid in the primary oxidation zone and bromine in an amount ranging from about 300 ppm to about 4500 ppm by weight with respect to the weight of the liquid in the primary oxidation zone;
   (b) routing said crude carboxylic acid composition to a low temperature post oxidation zone to form a low impurity stream; wherein said low impurity stream comprises FDCA; wherein said FFCA in said low impurity stream is less than 2000 ppm;
   (c) routing said low impurity slurry stream to a high temperature post oxidation zone to form secondary oxidation slurry stream; wherein said secondary oxidation slurry stream comprises FDCA; wherein said FFCA in said slurry is less than 1000 ppm; and wherein said the oxidizing temperature in said high temperature post oxidation zone is higher that the oxidizing temperature in the primary oxidation zone.

2. A process according to claim 1 wherein said oxidizing is accomplished in the presence of a catalyst system at a temperature of about 100° C. to about 220° C. to produce said carboxylic acid composition; and wherein said oxidizing temperature in said low temperature post oxidation zone is at a temperature of about 100° C. to about 220° C.

3. A process according to claim 2 where said oxidizing temperature in said high temperature post oxidation zone is at a temperature of about 115° C. to about 235° C.

4. A process according to claim 1 wherein said oxidizable raw material stream comprises at least one compound selected from the group consisting of 5-(hydroxymethyl)furfural (5-HMF) 5-HMF esters (5-R(C)OCH2-furfural where R=alkyl, cycloalkyl and aryl), 5-HMF ethers (5-R'OCH2-furfural, where R'=alkyl, cycloalkyl and aryl), and wherein the yield of furan-2,5-dicarboxylic acid is greater than 80%.

5. A process according to claim wherein said oxidizable raw material stream comprises at least one selected from the group consisting of 5-(hydroxymethyl)furfural (5-HM), 5-HMF esters (5-(CO)OCH2-furfural where R=alkyl, cycloalkyl and aryl), 5-HMF ethers (5-R'OCH2-furfural, where R'=alkyl, cycloalkyl and aryl), and wherein the yield of furan-2,5-dicarboxylic acid is greater than 90%.

6. A process according to claim 1 wherein said oxidizable raw materiel stream comprises at least one selected from the group consisting of 5-(hydroxymethyl)furfural (5-HMF), 5-HMF esters (5-R(CO)OCH2-furfural where R=alkyl, cycloalkyl and aryl), 5-HMF ethers (5-R'OCH2-furfural, where R'=alkyl, cycloalkyl and aryl), and wherein the yield of furan-2,5-dicarboxylic acid is greater than 95%.

7. A process according to claim 6 where the oxidizing is said high temperature post oxidation zone and said low temperature post Oxidation zone is within 10 degrees of each.

8. A process according to claim 7 where the oxidizing is said high temperature post zone is greater than 10 degrees of the oxidizing is said primary oxidation zone.

9. A process according to claim 8 wherein said oxidizable raw material stream comprises at least one compound selected from the group consisting of 5-(hydroxymethyl)furfural (5-HMF), 5-HMF esters (5-R(CO)OCH2-furfural where R=alkyl, cycloalkyl and aryl), and 5-HMF ethers (5-R'OCH2-furfural, where R'=alkyl, cycloalkyl and aryl), and wherein the yield of furan-2,5-dicarboxylic acid is greater than 90%.

10. A process according to claim 8 wherein said oxidizable raw material stream comprises at least one compound selected from the group consisting of 5-(hydroxymethyl)furfural (5-HMF), 5-HMF esters (5-R(CO)OCH2-furfural where R=alkyl, cycloalkyl and aryl), and 5-HMF ethers (5-R'OCH2-furfural, where R'=alkyl, cycloakyl and aryl), and wherein the yield of furan-2,5-dicarboxylic acid is greater than 95%.

11. A process according to claim 10 wherein said primary oxidation zone & low and high post comprises a catalyst system wherein said catalyst system comprises cobalt in a range from about 700 ppm to about 4500 ppm with respect to the weight of the liquid in the primary oxidation zone, manganese in an amount ranging from about 20 ppm to about 400 ppm by weight with respect to the weight of the liquid in the primary oxidation zone and bromine in an amount ranging from about 700 ppm to about 4000 ppm by weight with respect to the weight of the liquid in the primary oxidation zone.

* * * * *